April 20, 1943. J. M. REINECKE Plant Pat. 576
AVOCADO TREE
Filed Nov. 24, 1943
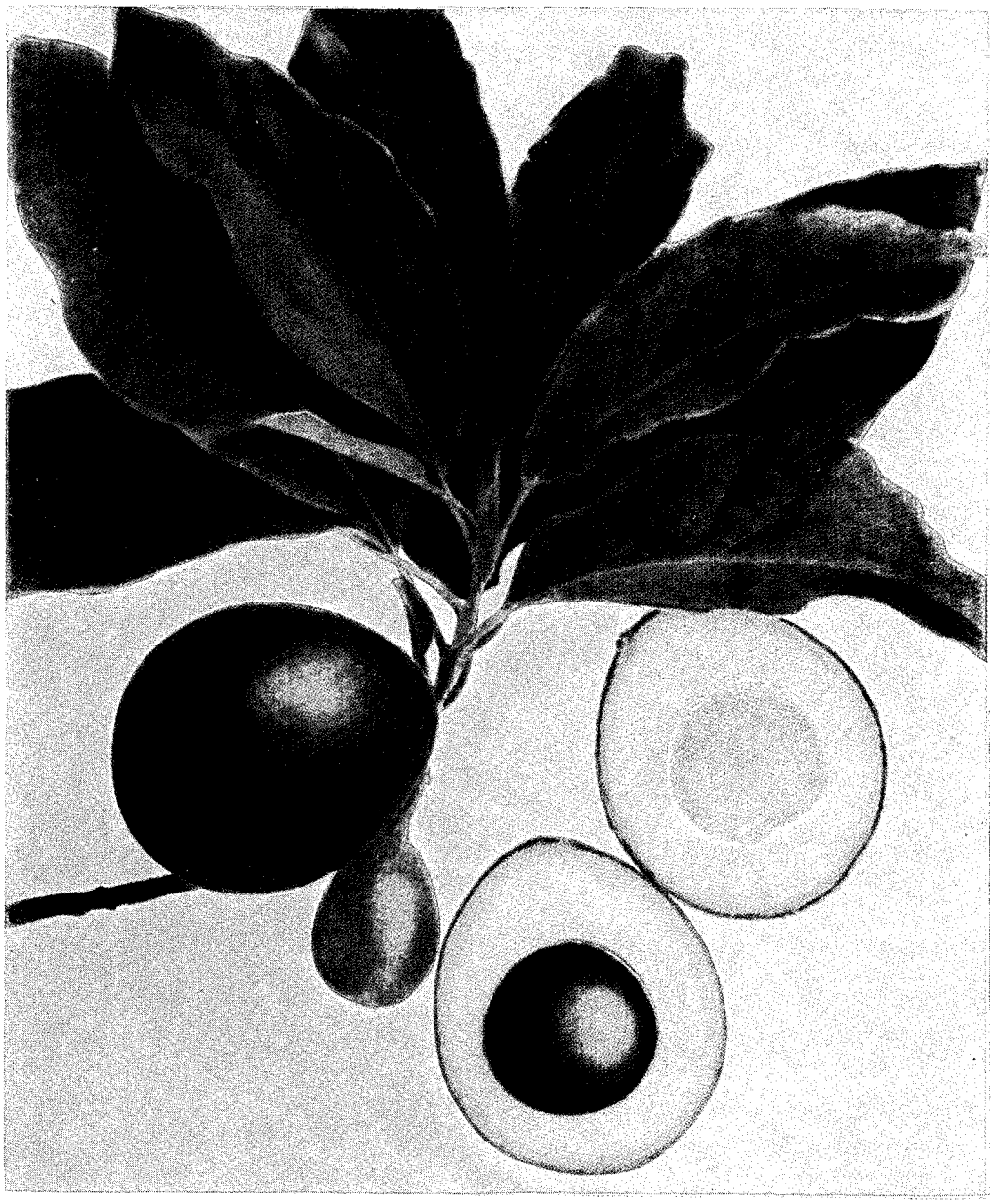
Inventor
J. M. Reinecke
By Robert Robb
Attorneys Patented Apr. 20, 1943

Plant Pat. 576

UNITED STATES PATENT OFFICE

576

AVOCADO TREE

John Martin Reinecke, San Diego, Calif., assignor to Armstrong Nurseries, Inc., Ontario, Calif., a corporation of California Application November 24, 1941, Serial No. 420,306

1 Claim. (Cl. 47—62)

The present discovery relates to a new and distinct variety of avocado tree originating as a chance seedling by the planting of an open pollenated seed of the Linscott avocado which was growing near a Nabal tree.

The tree was planted for the purpose of serving as a windbreak, but turned out to be a very worthwhile commercial variety because of its novel characteristics which are hereinafter set forth both generally and specifically.

Among its primary distinctive characters may be mentioned its extreme quantity of fruit borne in a very heavy crop season, alternating with a moderately heavy crop the following season, similar to the habit of the well-known Nabal variety before mentioned, except as to the much larger crop on the alternate years and the superior quality of the fruit of the present variety. This superior quality of fruit is evidenced by its high average oil content and its nutty flavor.

Additionally, the present variety possesses an attractive green skin and ovoid shape, a decided resistance to discoloration of the flesh after the fruit is cut, a later blooming date, compared with other varieties grown under comparable conditions, a vigorous habit of growth, an even ripening of the fruit qualities as compared with other avocados, and a semi-thick skin as compared with other varieties lacking anise scent.

By asexual reproduction the characteristics of the new variety have been found to be established.

The following is a detail description of the new variety, color terminology being in accord with Ridgway's Color Standard:

Observations made of tree grown in San Diego, California.

Dates first and last picking—June 1 to September 1 when picked in proper stage for marketing. Fruits frequently hang on through September.

Tree: Medium size; medium vigorous; upright; fairly dense; round-topped; half hardy with respect to other avocado varieties; very productive; from year to year alternates between very heavy and medium heavy crops of fruit.

*Trunk.*—Medium stocky.

*Branches.*—Medium slender; smooth; between Lettuce Green, Plate V, and Calla Green, Plate V. Newly hardened terminal growth—near Courge Green, Plate XVII. *Tomentum*—pubescence only on areas in the region of the termination of one growth cycle and the origin of another.

*Leaves.*—Length—variable up to nine inches. Width—variable up to four inches. Size—large—average. *Shape*—ovate, usually broadly cuneate at the base to lanceolate-cuneate, sometimes oblong. Thin. Mature leaf, upper side—near Dark Dull Yellow Green, Plate XXXI. Midrib of upper leaf surface near Pale Dull Green Yellow, Plate XVII, at base blending to near Light Grape Green, Plate XLI, which is usually maintained to apex. Veins near Light Grape Green, Plate XLI. Mature leaf, under side—near Pois Green, Plate XLI, much net-veined with near Vetiver Green, Plate XLVII. Large veins near Deep Sea Foam Green, Plate XXXI, blending gradually toward margin to near Vetiver Green, Plate XLVII. Color of midrib near Chrysolite Green, Plate XXX. Vein-like margin around under side of leaf near Vetiver Green, Plate XLVII. Freshly torn leaf—does not have anise scent. *Petiole*—medium long; medium thick; grooved on upper side with fine woolly pubescence. Under side smooth with very sparse, if any, pubescence. Color — between Calliste Green, Plate VI, and Courge Green, Plate XVII.

*Flowers.*—Dates first and full bloom—approximately the last week in April continuing into May; late compared with other varieties.

Fruit: Maturity when described—ripe; August, 1941.

*Size.*—Slightly variable; medium large. *Axial diameter*—four to four and one-half inches. *Transverse diameter*—three and five-eighths to four inches. *Weight*—nine to fifteen ounces.

*Form.*—Uniform; usually symmetrical; sometimes unsymmetrical; broadly obovoid. *Base*—obtuse, sometimes slightly oblique. *Apex*—rounded; very slightly depressed around pistil point. *Neck*—none. *Pistil point*—slightly apical.

*Stem.*—*Length*—approximately four inches; medium stout; pubescent. *Color*—near Calliste Green, Plate VI, changing gradually to between Courge Green, Plate XVII, and Deep Chrysolite Green, Plate XXXI, at point of attachment to fruit.

*Skin.*—Medium thick; tough; free; smooth; leathery yielding when flesh softens under strong pressure of thumb. *Tendency to crack*—none. *Color of skin of mature fruit*—between Ivy Green, Plate XXXI, and Yew Green, Plate XXXI, with occasional blending or shadings of Cress Green, Plate XXXI. Skin surface is dotted with minute dots of near Chrysolite Green, Plate XXXI, usually changing gradually about half way toward apex to woody dots of between Rood's Brown, Plate XXVIII, and Pecan Brown, Plate XXVIII. Some slight grittiness on inside of skin.

*Flesh.—Color* (from skin toward center)—region next to skin approximately ⅛" colored near Bice Green, Plate XVII, extending throughout the entire area of the flesh surface but blending gradually along this narrow margin, on both sides, to near Lumiere Green, Plate XVII, at extreme base. The green margin changes abruptly toward the center of the fruit to near Straw Yellow, Plate XVI, which in turn blends gradually to between Straw Yellow, Plate XVI, and Pinard Yellow, Plate IV, to edge of seed cavity. *Surface of seed cavity*—between Pinard Yellow, Plate IV, and Straw Yellow, Plate XVI. *Texture*—fine. *Fibres*—very few; fine; tender; the flesh is remarkably free from fibres. The few existent are tender and thin. They are nearly the same color as the flesh but may be seen on close observation. *Ripens*—even. *Maturity season*—June 1 to September 1. *Flavor*—nutty; rich; free from sweetness, bitterness, and soapiness. *Aroma*—distinct; sweet; nutty when first cut. *Eating quality*—excellent. *Oil content*—23.85% July 10, 1940; 16.61% April 21, 1941, and 19.85% July 10, 1941.

*Seed.—Size*—medium large; length 1⅝ to 1⅞ inches; breadth 1¾ to 2 inches; weight 1½ to 2½ ounces. *Form*—globose. *Base*—rounded; truncate at hilum. *Hilum*—broad. *Apex*—round to broadly ovoid. *Sides*—equal. *Surface*—smooth; seed coat adheres to the seed when removed from a ripened fruit. *Color of seed surface* (color of seed surface when dry—two to three hours from time of extraction): hilum near Pinkish-Buff, Plate XXIX, much dotted or speckled with minute dots of near Cinnamon, Plate XXIX. Dots become almost massed toward center of hilum. Hilum bordered irregularly with near Blackish Brown (1), Plate XLV, which blends abruptly but irregularly, to between Sayal Brown, Plate XXIX, and Cinnamon, Plate XXIX, this blending covering the greater part of the seed surface. Seed surface much netted with shallow fissures between Pinkish Buff, Plate XXIX, and Cinnamon, Plate XXIX. Apex heavily massed with specks or dots of between Pinkish-Buff, Plate XXIX, and Pale Ochraceous Buff, Plate XV.

Description of immature fruit set for crop succeeding mature fruits described herein picked from tree at the same time.

*Size.—Axial diameter*—1⅝ *inches. Transverse diameter*—1⅜ inches. *Weight*—one ounce.

*Form.*—Symmetrical; broadly obovoid; sometimes widely, sometimes narrowly grooved and ridged from base to apex. *Base*—obtuse, sometimes oblique. *Apex*—rounded. *Neck*—none. *Pistil point*—slightly apical.

*Stem.—Length*—approximately 3¾ inches; comparatively medium stout; pubescent. *Color*—near Calliste Green, Plate VI, changing gradually to between Courge Green, Plate XVII, and Deep Chrysolite Green, Plate XXXI, at point of attachment to fruit.

*Skin.*—Thin; 1/24 of an inch; comparatively medium thick; comparatively medium tough; tenacious to flesh; rough; leathery. *Color of skin of small immature fruit*—between Light Cress Green, Plate XXXI, and Cress Green, Plate XXXI, with many, minute, almost unnoticeable dots between Chrysolite Green, Plate XXXI, and Deep Chrysolite Green, Plate XXXI, grouped at apex.

Use: Market; local; dessert; culinary.

Keeping quality: Excellent; has long keeping qualities in both common and cold storage; cut surface remains bright and attractive for six to eight hours or more after cutting.

Shipping quality: Excellent.

I claim:

A new and distinct variety of avocado tree, characterized as to novelty by its habit of vigorous growth and late blooming; the ripening of the fruit qualities; its habit of bearing very heavy crops alternating with moderately heavy size crops; the superior quality of the fruit evidenced by high average oil content and nutty flavor; attractive semi-thick green skin; and resistance to discoloration of the flesh after cutting, substantially as shown and described.

JOHN MARTIN REINECKE.